United States Patent
Alard et al.

(10) Patent No.: US 9,757,325 B2
(45) Date of Patent: Sep. 12, 2017

(54) SKINCARE AND/OR MAKE-UP METHOD PROVIDING PROTECTION AGAINST UV RAYS

(71) Applicant: LVMH RECHERCHE, Saint Jean de Braye (FR)

(72) Inventors: Valerie Alard, Orleans (FR); Beatrice Beaufrere-Seron, Olivet (FR); Eric Perrier, Les Cotes D'arey (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 289 days.

(21) Appl. No.: 14/364,521

(22) PCT Filed: Dec. 10, 2012

(86) PCT No.: PCT/FR2012/052860
§ 371 (c)(1),
(2) Date: Jun. 11, 2014

(87) PCT Pub. No.: WO2013/088046
PCT Pub. Date: Jun. 20, 2013

(65) Prior Publication Data
US 2014/0341823 A1 Nov. 20, 2014

(30) Foreign Application Priority Data
Dec. 12, 2011 (FR) .................................... 11 61461

(51) Int. Cl.
| | | |
|---|---|---|
| *A61Q 17/04* | (2006.01) | |
| *A61K 8/02* | (2006.01) | |
| *A61K 8/97* | (2017.01) | |
| *A61Q 1/02* | (2006.01) | |
| *A61K 8/06* | (2006.01) | |
| *A45D 40/00* | (2006.01) | |
| *A61K 8/19* | (2006.01) | |
| *A61K 8/25* | (2006.01) | |
| *A61K 8/26* | (2006.01) | |
| *A61K 8/29* | (2006.01) | |
| *A61K 8/34* | (2006.01) | |
| *A61K 8/35* | (2006.01) | |
| *A61K 8/37* | (2006.01) | |
| *A61K 8/49* | (2006.01) | |
| *A61K 8/58* | (2006.01) | |
| *A61K 8/60* | (2006.01) | |
| *A61K 8/81* | (2006.01) | |
| *A61Q 19/00* | (2006.01) | |
| *A61Q 19/02* | (2006.01) | |
| *A61Q 19/08* | (2006.01) | |

(52) U.S. Cl.
CPC ................ *A61K 8/97* (2013.01); *A45D 40/00* (2013.01); *A61K 8/022* (2013.01); *A61K 8/062* (2013.01); *A61K 8/19* (2013.01); *A61K 8/25* (2013.01); *A61K 8/26* (2013.01); *A61K 8/29* (2013.01); *A61K 8/345* (2013.01); *A61K 8/35* (2013.01); *A61K 8/37* (2013.01); *A61K 8/4973* (2013.01); *A61K 8/585* (2013.01); *A61K 8/602* (2013.01); *A61K 8/8111* (2013.01); *A61K 8/8147* (2013.01); *A61Q 1/02* (2013.01); *A61Q 17/04* (2013.01); *A61Q 19/007* (2013.01); *A61Q 19/02* (2013.01); *A61Q 19/08* (2013.01); *A61K 2800/31* (2013.01); *A61K 2800/884* (2013.01)

(58) Field of Classification Search
CPC ............................... A61K 8/022; A61Q 17/04
See application file for complete search history.

(56) References Cited

U.S. PATENT DOCUMENTS

2004/0086474 A1* 5/2004 Rabe ........................ A61K 8/06
424/63

FOREIGN PATENT DOCUMENTS

JP 2008214267 A * 9/2008

OTHER PUBLICATIONS

Harry's Cosmeticology. Ed. M.M. Reiger. 8th ed. 2000, pp. 421 and 523-543.*
CAS Registry No. 541-02-6 (Nov. 16, 1984).*
CAS Registry No. 5466-77-3 (Nov. 16, 1984).*
Herzog, Bernd, et al. "New UV Absorbers for Cosmetic Sunscreens—A Breakthrough for the Photoprotection of Human Skin." CHIMIA 58.7/8 (2004): 554-559.*
CAS Registry No. 4065-45-6 (Nov. 16, 1984).*
Database GNPD [Online] MINTEL; May 2010, "1-2-3 Step Whitening Value Set", XP002680800.
Database GNPD [Online] MINTEL; May 2010, "UV Special Care Set", XP002680801.
Database GNPD [Online] MINTEL; Oct. 2010, "Globe-Trotter Travel Vanity Case", XP002680802.

(Continued)

*Primary Examiner* — Bethany Barham
*Assistant Examiner* — Peter Anthopolos
(74) *Attorney, Agent, or Firm* — Hamre, Schumann, Mueller & Larson, P.C.

(57) ABSTRACT

A method for protecting the skin against UV rays uses at least two cosmetic skincare and/or make-up compositions, and comprises applying a first layer of a first cosmetic composition comprising an oil phase and, optionally, an aqueous phase, followed by applying, on the first layer, a second layer of a second anhydrous composition comprising at least 70 wt.-% powders selected from among fillers and pigments, and an oil phase. At least one of the two compositions contains at least one UV filter, preferably a liposoluble UV filter. The first composition may be a make-up foundation or skincare base. The second composition may be a loose or compact powder.

4 Claims, No Drawings

(56) References Cited

OTHER PUBLICATIONS

Database GNPD [Online] MINTEL; Aug. 2011, "The Illuminating Powder", XP002681696.
Database Gnpd [Online] MINTEL; Apr. 2010, "The SPF 30 UV Protecting Fluid", XP002681697.
Database GNPD [Online] MINTEL; Jul. 2008, "Baby's Outing Pack", XP002680803.
Database GNPD [Online] MINTEL; Sep. 2007, "Powder Prickly Heat", XP002681698.
Colipa, CTFA SA, JCIA and CTHA: "International Sun Protection Factor (SPF) Test Method"; Colipa Guidelines, May 2006 (http://www.colipa.eu/publications-colipa-the-european-cosmetic-cosmetics-association, 46 pages.

* cited by examiner

SKINCARE AND/OR MAKE-UP METHOD PROVIDING PROTECTION AGAINST UV RAYS

The subject of the invention is a skincare and/or make-up method comprising the successive application of at least two compositions, one onto the other. This method makes it possible to reconcile daily protection against UV rays and good sensory properties, such as the absence of a tacky or greasy sensation upon application.

START OF THE ART

The effectiveness of a sun composition for the skin is usually reflected by a protective index or a sun protection factor (abbreviated as SPF). The SPF is defined by the ratio of the amount of energy required to cause the beginning of erythema on skin protected by a UV-radiation-screening agent, and the amount of energy required to cause the beginning of erythema on unprotected skin. The higher the SPF value measured, the higher the level of protection conferred by the product against ultraviolet radiation. In order to achieve significant levels of effectiveness, those skilled in the art are commonly led to introduce photoprotective agents in a large amount, all the more so if the required level of effectiveness is high.

Generally, cosmetic compositions intended for photoprotection of the skin contain organic and/or inorganic UV-screening agents which operate, depending on their chemical nature and their physical properties, by absorption, reflection or scattering of UV radiation. There are actual sun protection products with a high protective index, particularly indicated for long and intensive exposures to the sun, which are often occasional in nature. These sun products exist in particular in the form of a milk, a cream, a spray, a stick or impregnated wipes. These products can make it possible to achieve very high levels of photoprotection.

In addition to the risks of burning, it has been possible to demonstrate that ultraviolet radiation causes extrinsic skin aging, linked to a gradual deterioration of cell functions subsequent to the degradation of the proteins of the cell, such as constituent proteins of the extracellular matrix and enzymes which participate in maintaining cell homeostasis. Ultraviolet rays in particular cause the formation of free radicals which act on the abovementioned structures, and cause inflammation and irritation.

As a result, consumers wish to protect themselves against the harmful effects of ultraviolet rays throughout the day and throughout the year, and no longer solely during periods of strong sunshine or in the event of prolonged exposure to the sun.

Sunscreens have thus been introduced into care or make-up products for more regular use, in particular daily use, in order to protect the skin against sunshine which is weak in intensity and short in duration, since this weak-intensity exposure has been proven to be a skin aging factor. Sometimes, these compositions contain smaller amounts of UV-screening agents, but these screening agents are all the same detrimental to the feel, texture and application qualities desired by consumers. There are thus on the market numerous care or make-up products which comprise screening agents against ultraviolet radiation (also called "UV-screening agents" in the present application), which are either physical screening agents (inorganic UV-screening agents) or chemical UV-screening agents (organic UV-screening agents).

PURPOSES OF THE INVENTION

One of the objectives of the formulator of cosmetic care or make-up products is to reconcile the amount of sunscreens introduced into the product, the protection that the product provides against UV rays, and the sensory properties of the product.

The method of the invention makes it possible to improve the protection of the skin against UV rays without increasing the amount of UV-screening agents required to obtain this protection, and, consequently, while preserving the satisfactory sensory properties for the products applied to the skin.

The method of the invention also makes it possible to provide a care product, a make-up product or a product which performs both the function of skincare and the function of skin make-up, of which the protection against UV rays is comparable to those of the care and make-up products of the prior art, and of which the sensory properties are improved. In particular, the inventors have found that, by superposing at least two particular products, the amount of liposoluble UV-screening agents required to obtain a given protection is less than the amount of liposoluble screening agents that it would be necessary to incorporate into a single composition in order to obtain the same level of sun protection.

The present invention does not relate to the field of sun protection creams of which the protective index is high and which must be able to be applied easily over large areas of skin. The invention relates instead to the field of care and make-up products which are used daily by consumers in order to obtain a cosmetic care and/or make-up effect independent of a sun protection effect.

The inventors have discovered, surprisingly, that it is possible to produce cosmetic bodily or facial skincare or make-up which retains its primary care or make-up functions without complete alteration of its sensory properties, while providing satisfactory sun protection.

The method of protection of the invention also makes it possible to produce skincare or skin make-up with a pleasant texture and a pleasant sensoriality, which also provides improved protection against ultraviolet radiation.

These effects are obtained by superposing at least two layers of different products, a first and then a second composition, the second composition essentially comprising powders and at least one organic UV-screening agent.

The application of a composition in powder form on the first deposit makes it possible to significantly improve the protection against ultraviolet rays, compared with the protection that would be obtained by the application of a single composition.

The method of the invention makes it possible to obtain a very high sun protection while applying products with a pleasant texture and a pleasant sensoriality, through the superposition of two products which, moreover, have specific cosmetic functions independent of the sun protection.

The protection against UV rays that is conferred by the successive application of the two compositions according to the method of the invention, measured for example by the SPF, is greater than the protection conferred by the application of each composition taken separately. It is also greater than the sum of the protections conferred by the separate application of each of the two compositions. Thus, the superposition of the two compositions does not lead to a simple addition of the effects produced by each composition taken individually, but indeed produces a synergistic effect which was not foreseeable by those skilled in the art.

DESCRIPTION OF THE INVENTION

Method of Application

Thus, the first subject of the present invention is a method for protecting the skin against UV rays using at least two cosmetic care and/or make-up compositions, comprising:
the application, to at least part of the bodily or facial skin, of at least a first layer of a first cosmetic composition comprising an oil phase and, optionally, an aqueous phase, followed by
the application, on said first layer, of at least a second layer of a second anhydrous composition comprising at least 70% by weight of powders selected from fillers and pigments, and an oil phase,
said method being characterized in that at least one of the two compositions contains at least one UV-screening agent.

In the method of the invention, the two compositions are not intended to be mixed prior to their application, or after their application to the skin. On the contrary, it is sought to superpose the deposits of each composition on the skin. Thus, the second composition is advantageously applied to the surface of the deposit of the first composition on the skin, and the person who applies the product does not seek—at the time of application of the second composition on the first—to ruin the integrity of the first layer, in order to preserve the cosmetic effect which is associated therewith. For example, when applying a powder on a foundation, the powder must not substantially ruin the deposit of foundation which hides the imperfections of the skin. In particular, the two compositions do not contain ingredients capable of chemically reacting with one another via the creation of covalent bonds.

The first composition and the second composition each perform, independently of one another, a specific function which is not modified by the superposition of their deposits. They may, in this respect, be used alone while providing a cosmetic effect desired by the consumer.

According to the method of the invention, the consumer or the beautician applies at least two deposits of successive cosmetic products which retain their integrity on the skin. The make-up or care result formed on the skin is not in the form of a single homogeneous layer after the application of the two compositions.

According to the method of the invention, the overall protective effect measured by the SPF value after application of the first composition and of the second composition is advantageously greater than the highest SPF value of each of said compositions; it is also advantageously greater than the sum of the SPF values of each of said compositions.

UV-Screening Agent

The UV-screening agent may be selected from organic UV-screening agents, inorganic UV-screening agents and mixtures thereof.

The UV-screening agent is preferably at least one liposoluble organic UV-screening agent, optionally as a mixture with an inorganic UV-screening agent.

The term "organic UV-screening agent" is intended to mean any organic compound which absorbs UV radiation in the wavelength range of from 280 nm to 400 nm. The UV-screening agent is preferably "liposoluble" in the sense that it can be dissolved in the molecular state in an oil, or can be dispersed in an oil in colloidal form or in micelle form.

Liposoluble Organic UV-Screening Agents

The liposoluble organic UV-screening agents may in particular be selected from various families of chemical compounds. Mention may in particular be made of para-aminobenzoic acid derivatives, salicylic derivatives, cinnamic derivatives, benzophenones and aminobenzophenones, anthranillic derivatives, dibenzoylmethane derivatives, [beta],[beta]'-diphenyl acrylate derivatives, benzylidenecamphor derivatives, phenyl-benzotriazole derivatives, triazine derivatives, bis-resorcinyl triazines, imidazoline derivatives, benzalmalonate derivatives, 4,4-diarylbutadiene derivatives, benzoxazole derivatives and merocyanine derivatives, and mixtures thereof.

Examples of para-aminobenzoic acid derivatives are ethyl PABA, ethyl dihydroxypropyl PABA and ethylhexyl dimethyl PABA. Salicylic derivatives are in particular the homosalate sold in particular under the name "Eusolex HMS®" by Rona/EM Industries; the ethylhexyl salicylate sold in particular under the name "Neo Heliopan OS®" by Symrise; the dipropylene glycol salicylate sold in particular under the name "Dipsal®" by Scher; or the TEA salicylate sold in particular under the name "Neo Heliopan TS®" by Symrise.

Among the salicylic derivatives, mention will be made of the homosalate sold in particular under the name Neo Heliopan® HMS; and the ethylhexyl salicylate sold in particular under the name Neo Heliopan® OS by Symrise.

Among the cinnamate derivatives, mention may in particular be made, in a nonlimiting manner, of: 2-ethylhexyl-p-methoxycinnamate, isopropyl-p-methoxy-cinnamate, isoamyl methoxycinnamate, cinoxate (2-ethoxyethyl-p-methoxycinnamate), diethanolamine methoxycinnamate, glyceryl 2-ethylhexanoate di-p-methoxycinnamate, and [4-bis(trimethylsiloxy)methylsilyl-3-methylbutyl]-3,4,5,-trimethoxycinnamate.

Among the cinnamate derivatives mentioned above, use will quite particularly be made of 2-ethylhexyl-p-methoxy-cinnamate also known as ethylhexyl methoxy-cinnamate or octyl methoxycinnamate (USAN name: octinoxate) sold under the tradenames Parsol MCX from the company DSM Nutritional Products and Uvinul MC 80 from the company BASF.

Among the benzophenone derivatives, mention will be made of benzophenone-1 sold under the tradename Uvinul® 400; benzophenone-2 sold under the tradename Uvinul D50; benzophenone-3 or oxybenzone sold under the tradename Uvinul® M40; benzophenone-6 sold under the tradename Helisorb 11; and benzophenone-8 sold under the tradename Spectrasorb® UV-24.

An aminobenzophenone is, for example, the n-hexyl 2-(4-diethylamino-2-hydroxybenzoyl)benzoate sold in particular under the tradename "Uvinul® A+" by BASF.

Among the anthranilic derivatives, mention will be made of the menthyl anthranilate sold in particular under the reference Neo Heliopan® MA by Symrise.

Among the dibenzoylmethane-derived UV-screening agents, mention may in particular be made, in a nonlimiting manner, of: 2-methyldibenzoylmethane, 4-methyl-dibenzoylmethane, 4-isopropyldibenzoylmethane, 4-(tert-butyl)dibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-(tert-butyl)-4'-methoxydibenzoylmethane, 2-methyl-5-isopropyl-4'-methoxydibenzoylmethane, 2-methyl-5-(tert-butyl)-4'-methoxy-dibenzoylmethane, 2,4-dimethyl-4'-methoxydibenzoylmethane and 2,6-dimethyl-4-(tert-butyl)-4'-methoxydibenzoyl methane.

Among the dibenzoylmethane derivatives mentioned above, use will quite particularly be made of 4-(tert-butyl)-

4'-methoxydibenzoylmethane also called butyl methoxy dibenzoylmethane (abbreviated as BMDBM, INCI name 1-[4-(1,1-dimethylethyl)-phenyl]-3-(4-methoxyphenyl)-1,3-propanedione and USAN name azobenzone) sold under the tradenames Parsol® 1789 from the company DSM Nutritional Products, or Eusolex® 9020 from the company Merck.

Two [beta],[beta]'-diphenyl acrylate derivatives are octocrylene, sold in particular under the tradename "Uvinul® N539" by BASF; and etocrylene, sold in particular under the tradename "Uvinul® N35" by BASF.

Examples of benzylidene camphor derivatives are 3-benzylidenecamphor; methylbenzylidenecamphor sold in particular under the name "Eusolex® 6300" by Merck; and polyacrylamidomethylbenzylidenecamphor.

As phenylbenzotriazole derivatives, mention may be made of the drometrizole trisiloxane sold in particular under the name "Silatrizole®" by Rhodia Chimie.

Among the triazine derivatives mention may be made of the ethylhexyl triazone sold in particular under the tradename "Uvinul® T150" by BASF; the diethylhexyl butamido triazone sold in particular under the tradename "Uvasorb® HEB" by Sigma 3V; 2,4,6-tris(dineopentyl 4'-am inobenzalmalonate)-s-triazine; 2,4,6-tris(diisobutyl 4'-amino-benzalmalonate)-s-triazine; 2,4-bis(dineopentyl 4'-aminobenzalmalonate)-6-(n-butyl 4'-aminobenzoate)-s-triazine; bis-ethylhexyloxyphenolmethoxyphenyltriazine and 2,4-bis-(n-butyl 4'-aminobenzoate)-6-(aminopropyltrisiloxane)-s-triazine.

A bis-resorcinyl triazine derivative is the bis-ethylhexyloxyphenolmethoxy-phenyltriazine sold in particular under the tradename "Tinosorb® S" by Ciba Geigy.

An imidazoline derivative is ethylhexyl dimethoxybenzylidene dioxoimidazoline propionate.

Benzalmalonate derivatives are polyorganosiloxanes comprising a benzalmalonate function, such as the polysilicone-15 sold in particular under the tradename "Parsol® SLX" by DSM Nutritional Products, Inc.; and dineopentyl 4'-methoxy-benzalmalonate.

A benzoxazole derivative is the 2,4-bis[5-(1-dimethylpropyl)benzoxazol-2-yl-(4-phenyl)imino]-6-(2-ethylhexy-Dimino-1,3,5-triazine sold in particular under the name Uvasorb® K2A by Sigma 3V.

A merocyanine derivative is octyl-5-N,N-diethylamino-2-phenysulfonyl-2,4-pentadienoate.

An example of a 4,4-diarylbutadiene derivative is 1,1-dicarboxy(2,2'-dimethyl-propyl)-4,4-diphenylbutadiene.

In the context of the present invention, a liposoluble organic screening agent is preferably selected from the following screening agents and mixtures thereof: ethylhexyl salicylate; octocrylene; ethylhexyl triazone; ethylhexyl methoxycinnamate; butyl methoxydibenzoylmethane; n-hexyl 2-(4-diethylamino-2-hydroxybenzoyl)benzoate; drometrizole trisiloxane; methylene bis-benzotriazolyl tetramethylbutylphenol; bis-ethylhexyloxyphenol methoxyphenyl triazine; benzophenone-3 or oxybenzone.

The UV-screening agent may be present in the first composition or in the second composition. The compositions may contain, independently of one another, a UV-screening agent of identical or different chemical nature.

Inorganic UV-Screening Agents

The UV-screening agent may comprise at least one inorganic UV-screening agent.

The term "inorganic UV-screening agent" is intended to mean any organic compound which absorbs UV radiation in the same wavelength range as previously indicated.

The inorganic UV-screening agents may be selected from metal oxide pigments having an average particle size generally between 5 nm and 100 nm, preferably between 10 nm and 50 nm, for instance titanium oxide (amorphous or crystallized in rutile and/or anatase form) or zinc oxide pigments.

The pigments may or may not be surface-treated.

The surface-treated pigments are pigments which have undergone one or more surface treatments of chemical, electronic, mechanochemical and/or mechanical nature with compounds as described, for example, in Cosmetics & Toiletries, February 1990, Vol. 105, p. 53-64, such as amino acids, beeswax, fatty acids, fatty alcohols, anionic surfactants, lecithins, sodium, potassium, zinc, iron or aluminum salts of fatty acids, metal (titanium or aluminum) alkoxides, polyethylene, silicones, proteins (collagen, elastin), alkanolamines, silicon oxides, metal oxides or sodium hexametaphosphate.

The silicones used for the treatment of the pigments are, for example, selected from the group containing alkylsilanes, polydialkylsiloxanes and polyalkyl-hydrosiloxanes.

Of course, the metal oxide pigments, before their treatment with silicones, may have been treated with other surface agents, in particular with cerium oxide, alumina, silica, aluminum compounds, silicon compounds, or mixtures thereof.

In the context of the invention, it is preferred to use amorphous or crystallized titanium oxide in rutile and/or anatase form as inorganic UV-screening agent.

The content of inorganic UV-screening agent in the first composition is, for example, less than or equal to 25% by weight, advantageously between 2% and 20% by weight, more particularly between 3% and 10% by weight, relative to the total weight of the first composition.

The content of inorganic UV-screening agent in the second composition is, for example, less than or equal to 25% by weight, advantageously between 2% and 20% by weight, more particularly between 3% and 10% by weight, relative to the total weight of the second composition.

According to one embodiment of the invention, the first composition is free of inorganic screening agent and of organic screening agent, and the second composition comprises at least one organic screening agent and, optionally, at least one inorganic screening agent.

According to another embodiment of the invention, the first composition comprises at least one organic screening agent, and the second composition comprises at least one organic screening agent and, optionally, at least one inorganic screening agent.

The content of UV-screening agent in the first composition is, for example, less than or equal to 40% by weight, advantageously between 5% and 30% by weight, more particularly between 10% and 20% by weight, relative to the total weight of the first composition.

The content of UV-screening agent in the second composition is, for example, less than or equal to 30% by weight, advantageously between 1% and 20% by weight, more particularly between 5% and 15% by weight, relative to the total weight of the second composition.

According to one embodiment of the invention, the first composition comprises:
  from 5% to 8% by weight of octyl methoxycinnamate relative to the total weight of the first composition, and, optionally, from 0.5% to 3% by weight of benzophenone-3 relative to the total weight of the first composition, or from 4% to 8% by weight of octyl methoxycinnamate relative to the total weight of the first composition and, optionally, at least one inorganic UV-screening agent, preferably from 4.5% to 15% by weight of a nano titanium relative to the total weight of the first composition.

According to one embodiment of the invention, the second composition comprises from 4% to 8% by weight of octyl methoxycinnamate relative to the total weight of the second composition and, optionally, at least one inorganic UV-screening agent, preferably from 4.5% to 15% of a nano titanium relative to the total weight of the second composition.

Oil Phases of the Two Compositions

The first composition preferably contains at least one oil phase, preferably a single oil phase. The second composition also preferably contains at least one oil phase, preferably a single oil phase.

In this embodiment, when the first or the second composition contains a liposoluble UV-screening agent, each of said oil phases and/or the mixture of said oil phases advantageously solubilizes the liposoluble organic UV-screening agent.

The term "oil phase" is intended to mean an oil or a mixture of oils which are miscible with one another. For the purpose of the invention, the term "oil" is intended to mean a fatty substance which is water-insoluble, which is liquid at 25° C. and 0.1 MPa, and which is preferably non-volatile, having a non-zero vapor pressure at 25° C. and 0.1 MPa of less than 2.6 Pa, preferably less than 0.13 Pa.

In one embodiment, the first composition and the second composition each contain an oil phase. The two oil phases of the compositions are preferably miscible with one another. When the UV-screening agent is a liposoluble organic UV-screening agent, said screening agent is advantageously soluble in each of the oil phases of the two compositions.

The miscibility of the two oil phases with one another can be evaluated according to the following protocol. The first oil phase is weighed out in a beaker and then the second oil phase is added to the beaker according to the weight ratio of the oil phases of each formula. Stirring is carried out for 5 minutes and then the whole mixture is conditioned in a 120 ml sample tube. It is left to stand for 24 hours at 25° C. After standing for 24 hours, the mixture is visibly clear and homogeneous, it is considered that the two phases are miscible.

It is also preferred for the oil phase of the first composition and the oil phase of the second composition to contain oils which are miscible with one another. The protocol for evaluating the miscibility of the oils of the oil phase may be identical to that previously described.

The oil phase of the first composition and/or the oil phase of the second composition preferably contain at least one polar oil. The term "polar oil" is intended to mean an oil which contains at least one, preferably at least two, oxygen atoms, or conjugated double bonds.

The oil is preferably selected from aliphatic monoesters and diesters, nonhydroxylated aromatic esters, aliphatic carbonates and phenyl silicones.

The term "aliphatic ester" is intended to mean a compound consisting of carbon atoms, of hydrogen atoms and of at least one carboxyl group COO. The term "monoester" is intended to mean a compound comprising a COO group, and the term "diester" is intended to mean a compound comprising two COO groups.

The term "hydroxylated ester" is intended to mean a compound comprising at least one COO group and at least one OH group.

In another embodiment, an ester selected from aliphatic monoesters and diesters is preferred.

As polar oils, mention may, for example, be made of aliphatic monoesters and diesters, in particular i) monoesters of a saturated or unsaturated, preferably saturated, linear or branched aliphatic carboxylic acid comprising from 8 to 20 carbon atoms and of an aliphatic monoalcohol comprising from 3 to 20 carbon atoms, ii) aliphatic diesters of an aliphatic dicarboxylic acid comprising from 4 to 10 carbon atoms and of a monoalcohol, monoesters of benzoic acid and of an aliphatic alcohol comprising from 8 to 20 carbon atoms, 2-ethylhexyl benzoate, 2-octyldodecyl benzoate, isostearyl benzoate, $C_{12}$-$C_{15}$ alkyl benzoate, triesters and tetraesters, such as esters of pentaerythritol, in particular pentaerythrityl tetraisosearate, esters of trimethylolpropane, in particular trimethylol-propane triisosearate, esters of citric acid, in particular tridecyl citrate, and tridecyl trimellitate, dialkyl carbonates in which the alkyl groups contain from 8 to 18 carbon atoms, such as dicaprylyl carbonate or di(2-ethylhexyl) carbonate, hydroxylated aliphatic monoesters or diesters such as i) esters of a hydroxylated aliphatic monocarboxylic or dicarboxylic acid comprising from 3 to 20 carbon atoms and of an aliphatic monoalcohol comprising from 6 to 20 carbon atoms, for example isostearyl lactate, octyl hydroxystearate, octyldodecyl hydroxystearate, cetyl lactate, myristyl lactate or diisostearyl malate, or ii) aliphatic monoesters and diesters of a polyol, in particular of diols and of triols, such as esters of an aliphatic monocarboxylic acid comprising from 3 to 20 carbon atoms and of an aliphatic diol or triol comprising from 3 to 20 carbon atoms, aromatic hydroxylated monoesters and diesters of a hydroxylated aromatic carboxylic acid and of an aliphatic monoalcohol comprising at least 10 carbon atoms, saturated or unsaturated aliphatic alcohols having from 8 to 26 carbon atoms, for instance octyldodecanol, octyldecanol, 2-butyloctanol, 2-hexyldecanol or 2-undecylpentadecanol, saturated or unsaturated aliphatic monocarboxylic acids having from 7 to 29 carbon atoms, such as oleic acid, linoleic acid, linolenic acid or isostearic acid, silicone oils comprising at least one alkoxy or phenyl group, which is pendant or at the end of the silicone chain, having from 2 to 24 carbon atoms, in particular phenyl trimethicone, phenyl dimethicones, phenyltrimethylsiloxydiphenylsiloxanes, diphenyl dimethicones, diphenylmethyldiphenyltrisiloxanes, 2-phenylethyltrimethyl siloxysilicates and polymethylphenylsiloxanes;

glycols, aliphatic ethers comprising more than 10 carbon atoms, triglycerides, for example sunflower oil, corn oil, soya oil, marrow oil, grapeseed oil, sesame oil, hazelnut oil, apricot oil, macadamia oil, arara oil, castor oil, avocado oil, jojoba oil, shea butter oil, caprylic/capric acid triglycerides, glyceryl triheptanoate, glyceryl trioctanoate, glyceryl tri(2-ethylhexanoate), glyceryl triisostearate, glyceryl triisononanoate, glyceryl trimyristate and glyceryl triisopalmitate, and mixtures thereof.

In one embodiment, it is preferable for the oil to be an ester selected from aliphatic monoesters and diesters.

According to another embodiment, the oil is a silicone oil comprising aromatic carbon-based groups.

Among the aliphatic monoesters and diesters, preference is given to esters comprising from 10 to 25 carbon atoms, preferably from 14 to 22 carbon atoms, for example esters of isononanoic acid, such as isononyl isononanoate, isodecyl isononanoate, 2-decylhexyl isononanoate, isostearyl isononanoate, cetearyl isononanoate or tridecyl isononanoate.

Mention may also be made of isopropyl myristate, 2-ethylhexyl palmitate, 2-octyldodecyl stearate, 2-octyldodecyl erucate, isostearyl isostearate, octyldodecyl stearoylstearate, isostearyl palmitate, isocetyl stearate, octyldodecyl myristate, triisostearyl trilinoleate, octyldodecyl neodecanoate, octyldodecyl octanoate, isobutyl stearate, isodecyl neopentanoate, octyldodecyl neopentanoate, 2-ethylhexyl isostearate, butyl isostearate, isopropyl palmitate, stearyl heptanoate, isopropyl stearate, isostearyl neopentanoate, isopropyl isostearate, cetyl octanoate (or palmityl octanoate), butyl stearate, hexyl laurate (or hexyl dodecanoate), ethyl laurate, decyl oleate, oleyl oleate, myristyl myristate, hexyldecyl di methyloctanoate, isocetyl isostearate, 2-hexyldecyl myristate, 2-heptylundecyl palmitate and cetyl 2-ethylhexanoate.

Among the esters of dicarboxylic acids, mention may also be made of di(2-ethylhexyl) sebacate, diisopropyl sebacate, di(2-ethyl-hexyl) succinate, di(2-hexyldecyl) adipate and di(2-undecylheptyl) adipate.

Among the monoesters and diesters of a polyol, mention may be made of diesters of an alkylene glycol with an aliphatic acid having from 6 to 20 carbon atoms, such as propylene glycol dioctanoate, neopentyl glycol diheptanoate and diethylene glycol diisononanoate; butylene glycol dicaprate/dicaprylate, propylene glycol dicaprate/dicaprylate, neopentyl glycol dicaprate, diethylene glycol diisononanoate, propylene glycol diisostearate, propylene glycol dipelargonate, propylene glycol dioctanoate, neopentyl glycol diheptanoate, tripropylene glycol dipivalate; and glyceryl monoalkanoates, such as glyceryl heptanoate, glyceryl octanoate and glyceryl decanoate.

The preferred polar oils of the first composition are $C_{12}$-$C_{15}$ alkyl benzoate and isodecyl neopentanoate.

The preferred oil of the second composition is phenyl trimethicone or hydrogenated polyisobutene.

Galenics of the First Composition

The first composition is preferably in the form of an emulsion containing an aqueous phase and an oil phase. The aqueous phase preferably represents at least 10% by weight, more preferably at least 15% by weight, of the weight of the first composition.

The first composition may or may not contain at least one UV-screening agent selected from organic UV-screening agents and inorganic UV-screening agents.

The first composition may contain a liposoluble organic UV-screening agent and, optionally, an inorganic screening agent.

The first composition is preferentially intended to be applied to the face and is preferably in the form of an oil-in-water or water-in-oil emulsion or an aqueous gel. The composition is, for example, in the form of a care cream, a lotion, a serum or a fluid for the face, a foundation, a milk, or a primer.

The first composition may also comprise at least one colorant, advantageously selected from pigments, liposoluble dyes and nacres. The pigments may be white or colored, inorganic and/or organic, and coated or uncoated. Among the pigments that can be used, mention is made of titanium dioxide which is optionally surface-treated, zirconium oxide, zinc oxide or cerium oxide, and also iron oxide or chromium oxide, manganese violet, ultramarine blue, chromium hydrate and ferric blue, carbon black, and dyeing lakes, in particular barium, strontium, calcium or aluminum lakes.

The nacres may be selected from white nacreous pigments such as mica coated with titanium or with bismuth oxychloride, colored nacreous pigments such as titanium mica with iron oxides, titanium mica in particular with ferric blue or chromium oxide, titanium mica with an organic pigment of the abovementioned type, and also nacreous pigments based on bismuth oxychloride.

The first composition of the invention may also comprise one or more hydrophilic organic UV-screening agents, such as the benzophenone-4 sold under the tradename "Uvinul® MS40" or alternatively methylene bis-benzotriazolyl tetramethyl-butylphenol, sold in solid form in particular under the tradename "Mixxim BB/100®" by Fairmount Chemical or in micronized form in an aqueous dispersion, in particular under the tradename "Tinosorb® M" by Ciba Specialty Chemicals.

The first composition of the invention may also comprise any additive normally used in the cosmetics industry, such as a solid filler, antioxidants, surfactants, preservatives, film-forming polymers, fragrances, cosmetic active agents, for instance emollients, moisturizers, vitamins, anti-aging agents, or lightening agents, and mixtures thereof.

The sun protection index of the first composition is preferably greater than 10. The sun protection factor SPF of the first composition is, for example, between 30 and 40.

Galenics of the Second Composition

According to one embodiment, the second composition contains at least one UV-screening agent, preferably a liposoluble organic UV-screening agent.

The second composition is, for example, in the form of a loose or compact powder which has a sun protection index, measured according to the SPF method, of less than or equal to 10, and preferably greater than 3. The second composition has, for example, an SPF of about 4.

The second composition advantageously contains the mixture of at least one organic screening agent and at least one inorganic screening agent.

The second composition is preferentially intended to be applied to the face and is preferably in the form of a loose or compact powder. It preferably contains at least 80%, more preferentially at least 90% by weight of powders selected from the fillers and pigments commonly used in the cosmetics industry.

The second composition is preferably anhydrous, in the sense that it contains less than 10% of water by weight, preferably less than 5% by weight, more preferably less than 3% by weight, of the weight of the composition.

The second composition advantageously contains fillers and pigments, which can be selected from inorganic pigments, organic pigments and nacreous pigments.

The inorganic pigments may be selected from iron oxides, in particular black, yellow, red and brown iron oxides; manganese violet; ultramarine blue; chromium oxides, in particular chromium oxide hydrate, ferric blue, and carbon black, and mixtures thereof.

Among the organic pigments, mention may in particular be made of the lakes obtained from dyes such as the dyes D&C Black No. 2, FD&C Blue No. 1, FD&C Green No. 3, D&C Green No. 5, D&C Orange No. 4, D&C Orange No.

5, D&C orange No. 10, D&C Red No. 3, D&C Red No. 6, D&C Red No. 7, D&C red No. 9, D&C red No. 13, D&C red No. 19, D&C Red No. 21, D&C Red No. 22, D&C Red No. 27, D&C Red No. 28, D&C Red No. 30, D&C Red No. 33, D&C Red No. 36, FD&C Red No. 40, FD&C Yellow No. 5, FD&C Yellow No. 6, D&C Yellow No. 10 and cochineal carmine.

The nacreous pigments are, for example, selected from mica coated with titanium oxide, titanium mica coated with iron oxide, titanium mica coated with ferric blue, titanium mica coated with chromium oxide, titanium mica coated with an organic pigment as previously described, and also pigments based on bismuth oxychloride.

The fillers may be inorganic or organic, and of any shape, platelet, spherical or oblong.

The fillers are selected in particular from inorganic fillers such as:
talc, preferably in the form of particles generally having dimensions of less than 40 μm;
micas of natural or synthetic origin having dimensions of from 2 to 200 μm, preferably from 5 to 70 μm, and a thickness of from 0.1 to 5 μm, preferably from 0.2 to 3 μm,
kaolin having particle sizes generally of less than 30 μm;
metal soaps derived from organic carboxylic acids having from 8 to 22 carbon atoms, preferably from 12 to 18 carbon atoms, for example zinc stearate, magnesium stearate or lithium stearate, zinc laurate, magnesium myristate, preferably in the form of particles having dimensions of less than 10 μm;
zinc oxides, titanium oxides; calcium carbonate; magnesium carbonate, magnesium hydrogen carbonate, silica, glass beads, ceramic beads;
and mixtures thereof.

It is also possible to use, as fillers, organic fillers such as:
crosslinked or noncrosslinked starches, for example corn, wheat or rice starches;
powders of expanded or nonexpanded, spheronized or nonspheronized, crosslinked or noncrosslinked synthetic polymers, for instance polyethylene powders, polyester powders (for example isophthalate or terephthalate), polyamide powders (for example poly-β-alanine powders and nylon powders, for instance those sold under the name Orgasol®), powders of poly(meth)acrylic acid or of poly(meth)acrylate, such as crosslinked methyl methacrylate powders, polyurethane powders such as copolymers of hexamethylene diisocyanate and of trimethylolhexyllactone sold under the names Plastic Powder® D-400 and Plastic Powder® D-800 by the company Toshiki, divinylbenzene-crosslinked polystyrene powders, silicone resin powders such as silsesquioxanes, or tetrafluoroethylene (Teflon®) powders;
and mixtures thereof.

The second composition may have various cosmetic uses, and in particular may serve as a foundation, a primer, a body make-up powder, a care powder, a face make-up powder, a blusher or face powder, an eyeshadow, a complexion illuminator, a bronzing powder, or a protective complexion powder.

The composition of the invention is preferably a loose make-up powder.

The application of the second composition can be carried out with a brush, in a spray, with a sponge or with a finger. It is preferably carried out with a brush.

Definition and Measurement of the Sun Protection Index

The level of sun protection conferred by each composition and also by the superposition of the two deposits of the compositions can be measured by various methods known to those skilled in the art, in vivo or in vitro.

The sun protection index of a composition can be measured according to the method of in vivo measurement of the sun protection factor (SPF) published by Colipa, CTFA SA, JCIA and CTHA in May 2006 (on the website http://www.colipa.eu/publications-colipa-the-european-cosmetic-cosmetics-association; "International Sun Protection Factor Test Method—2006"). According to these methods, the SPF of a composition is defined as the ratio between the irradiation time required to reach the erythema-forming threshold of skin to which the composition has been applied, and the time required to reach the erythema-forming threshold of bare skin. The method published by Colipa specifies the minimum conditions to be observed in order for the SPF measurement to reproducible and significant. The guidelines mention in particular the amount of composition which must be applied to the skin, and the irradiation lamp which must be used.

Other methods also exist for quantifying the level of protection conferred by a cosmetic product, for instance the PPD (Persistent Pigment Darkening) method, which measures the color of the skin observed 2 to 4 hours after exposure of the skin to UV-A rays (wavelengths of between 320 nm and 400 nm). This method has been used since 1996 by the Japanese Cosmetic Industry Association (JCIA) for UV-A labeling of products and by test laboratories in Europe and in the United States (Japan Cosmetic Industry Association—Technical Bulletin—Measurement Standards for UVA protection efficacy—Issued Nov. 21, 1995 and effective of Jan. 1, 1996). The UVAPPD protection factor (UVAPPD PF) corresponds to the ratio i) of the dose of UV-A radiation required in order for skin covered with cosmetic composition to reach the pigmentation threshold (MPPDp) to ii) the dose of UV-A radiation required in order for bare skin to reach the pigmentation threshold (MPPDnp).

In the context of the invention, it is preferable to measure the level of sun protection provided by the first composition, the second composition and the superposition thereof using a method which reproduces the protocol and the parameters recommended in the method described by Colipa in 2006, with the sole exception of the dose applied, which is chosen to be equal to 0.8 mg/cm$^2$.

Product

The second subject of the present invention is a cosmetic product comprising at least two cosmetic compositions packaged separately, in the same packaging,
the first cosmetic composition being intended to be applied to the skin and comprising an aqueous phase and an oil phase, which can in particular be in the form of a cream or a fluid, and
the second composition being intended to be applied on the first composition and comprising at least 70% by weight of powders selected from fillers and pigments,
at least one of the two compositions containing at least one UV-screening agent.

The second composition advantageously has an SPF of less than or equal to 10.

The first composition is, for example, a care cream, a care base or a foundation, while the second is a powder.

According to one preferred embodiment, the first composition is a water-in-oil or oil-in-water emulsion, which optionally contains pigments.

The first composition may comprise one or more active ingredients selected from moisturizing active ingredients, anti-aging active ingredients, antioxidant active ingredients and depigmenting active ingredients.

The second composition is advantageously a loose, pressed or compact powder.

Use of a Powder for Increasing the SPF of a Cream

The third subject of the present invention is the use of a second cosmetic composition comprising at least 70% by weight of powders selected from fillers and pigments, an oil phase and at least one liposoluble organic UV-screening agent, for use on a first composition which does not contain a UV-screening agent, in order to obtain a cosmetic result with improved sensory properties while obtaining a satisfactory level of daily protection of the skin against UV rays through the successive application of the first and then of the second composition to the skin.

Method for Increasing the SPF

The fourth subject of the present invention is a method for increasing the sun protection index of a first cosmetic composition containing an oil phase, and optionally an active ingredient, while preserving its sensory qualities, which method consists in applying the first composition to the skin so as to form a layer, and then in applying, on this layer, a second composition containing an oil phase, at least 70% by weight of fillers and pigments, and at least one liposoluble organic UV-screening agent.

The liposoluble organic UV-screening agent is preferably soluble in the mixture of the two oil phases of the two compositions. It may be in accordance with the description of said screening agent that was given above.

According to one embodiment, the second composition comprises at least one liposoluble organic UV-screening agent and, optionally, at least one inorganic UV-screening agent.

The first composition may comprise or may not comprise UV-screening agent.

The characteristics which have been described above in relation to the first composition and the second composition apply to the second, third and fourth subjects of the invention.

In the examples, all the percentages are given by weight, unless otherwise indicated, and the temperature is expressed in degrees Celsius unless otherwise indicated, and the pressure is atmospheric pressure, unless otherwise indicated.

Example: Measurement of the Sun Protection Index Resulting from the Method of the Invention The implementation of the invention requires two distinct compositions which are described successively hereinafter:

First Compositions

The following products were prepared.

The CARE BASE 1 contains 3% of benzophenone-3, 7.5% of octyl methoxycinnamate and 5% of treated nano titanium. Its SPF measured on 10 subjects according to the measurement protocol and conditions given in the method "International Sun Protection Factor Test Method—2006" published by Colipa is equal to 36.4+/−4.8.

The CARE BASE 2 does not contain UV-screening agents.

The first liquid foundation (FOUNDATION 1) contains 6% of octyl methoxycinnamate and 6% of treated nano titanium. The SPF value measured on 10 subjects according to the measuring protocol and conditions given in the method "International Sun Protection Factor Test Method—2006" published by Colipa is equal to 36.3+/−5.0.

The second foundation (FOUNDATION 2) does not contain UV-screening agents.

Their detailed composition is given hereinafter.

| CARE BASE 1 | |
| --- | --- |
| INCI name | % by weight |
| WATER | qs 100 |
| C12-15 ALKYL BENZOATE | 20.3 |
| METHYL TRIMETHICONE | 9.0 |
| ETHYLHEXYL METHOXYCINNAMATE | 7.5 |
| TREATED NANO TITANIUM | 5.0 |
| BUTYLENE GLYCOL | 5.0 |
| ETHYLENE/ACRYLIC ACID COPOLYMER | 5.0 |
| GLYCEROL | 4.3 |
| CETYL PEG/PPG-10/1 DIMETHICONE | 4.0 |
| BENZOPHENONE-3 | 3.0 |
| PHENOXYETHANOL | 0.85 |
| PIGMENTS AND NACRES | 8.7 |
| CAPRYLYL GLYCOL | 0.5 |
| POLYHYDROXYSTEARIC ACID | 0.45 |
| *BETULA ALBA* JUICE EXTRACT | 0.4 |
| TETRASODIUM EDTA | 0.2 |
| KHARISMAL | 0.1 |
| STEARYL GLYCYRRHETINATE | 0.1 |

| CARE BASE 2 | |
| --- | --- |
| INCI name | % by weight |
| C12-15 ALKYL BENZOATE | 35.5 |
| WATER | qs 100 |
| METHYL TRIMETHICONE | 9.0 |
| BUTYLENE GLYCOL | 5.1 |
| ETHYLENE/ACRYLIC ACID COPOLYMER | 5.0 |
| GLYCEROL | 4.3 |
| CETYL PEG/PPG-10/1 DIMETHICONE | 4.0 |
| PHENOXYETHANOL | 0.8 |
| PIGMENTS AND NACRES | 8.6 |
| CAPRYLYL GLYCOL | 0.5 |
| *BETULA ALBA* EXTRACT | 0.4 |
| TETRASODIUM EDTA | 0.2 |
| KHARISMAL | 0.1 |
| STEARYL GLYCYRRHETINATE | 0.1 |
| BENZYL ACETATE | <0.1 |
| EXTRACT OF MALLOW (*MALVA SYLVESTRIS*) | <0.1 |

| FOUNDATION 1 | |
| --- | --- |
| INCI name | % by weight |
| WATER | qs 100 |
| CYCLOPENTASILOXANE | 21.6 |
| TREATED NANO TITANIUM | 7.0 |
| ETHANOL | 9.4 |
| ETHYLHEXYL METHOXYCINNAMATE | 6.0 |
| CETYL PEG/PPG-10/1 DIMETHICONE | 3.5 |
| ASCORBYL GLUCOSIDE | 2.1 |
| ACRYLATES/DIMETHICONE COPOLYMER | 2.0 |
| ISODECYL NEOPENTANOATE | 1.7 |
| PIGMENTS AND NACRES | 12.0 |
| BORON NITRIDE | 1.5 |
| CYCLOHEXASILOXANE | 1.1 |
| SORBITAN SESQUIOLEATE | 1.0 |
| SODIUM CITRATE | 0.5 |
| DISTEARDIMONIUM HECTORITE | 0.4 |
| PHENOXYETHANOL | 0.3 |
| SODIUM HYDROXIDE | 0.2 |
| TETRASODIUM EDTA | 0.2 |
| *BETULA ALBA* EXTRACT | 0.2 |

FOUNDATION 1 -continued

| INCI name | % by weight |
|---|---|
| KHARISMAL | 0.1 |
| PROPYLENE CARBONATE | 0.1 |

FOUNDATION 2

| INCI name | % by weight |
|---|---|
| WATER | qs 100 |
| CYCLOPENTASILOXANE | 21.6 |
| ISODECYL NEOPENTANOATE | 14.8 |
| PIGMENTS AND NACRES | 12.0 |
| ETHANOL | 9.4 |
| CETYL PEG/PPG-10/1 DIMETHICONE | 3.5 |
| ASCORBYL GLUCOSIDE | 2.1 |
| ACRYLATES/DIMETHICONE COPOLYMER | 2.0 |
| BORON NITRIDE | 1.5 |
| CYCLOHEXASILOXANE | 1.1 |
| SORBITAN SESQUIOLEATE | 1.0 |
| SODIUM CITRATE | 0.5 |
| DISTEARDIMONIUM HECTORITE | 0.4 |
| PHENOXYETHANOL | 0.3 |
| SODIUM HYDROXIDE | 0.2 |
| TETRASODIUM EDTA | 0.2 |
| *BETULA ALBA* EXTRACT | 0.2 |
| KHARISMAL | 0.1 |
| PROPYLENE CARBONATE | 0.1 |
| BENZYL ACETATE | <0.1 |

Second Compositions

The following compositions were prepared.

The POWDER 1 contains 5% of octyl methoxycinnamate and 4.5% of treated nano titanium. Its SPF measured on 10 subjects according to the measuring protocol and conditions given in the method "International Sun Protection Factor Test Method—2006" published by Colipa is equal to 6.3+/−1.1.

The POWDER 2 contains 9.5% of octyl methoxycinnamate.

Their detailed composition is given hereinafter.

POWDER 1

| INCI name | % by weight |
|---|---|
| TALC | qs 100 |
| SYNTHETIC FLUORPHLOGOPITE | 25.3 |
| SILICA | 12 |
| ETHYLENE/ACRYLIC ACID COPOLYMER | 5.0 |
| ETHYLHEXYL METHOXYCINNAMATE | 5.0 |
| TREATED NANO TITANIUM | 4.5 |
| BORON NITRIDE | 4.0 |
| MAGNESIUM ASCORBYL PHOSPHATE | 3.2 |
| PIGMENTS AND NACRES | 7.2 |
| POLYMETHYL METHACRYLATE | 2.0 |
| PENTYLENE GLYCOL | 1.0 |
| C9-13 FLUOROALCOHOL | 0.9 |
| WATER | 0.85 |
| STEARIC ACID | 0.6 |
| SODIUM DEHYDROACETATE | 0.45 |
| TETRASODIUM EDTA | 0.2 |
| DIMETHICONE/METHICONE COPOLYMER | 0.2 |

POWDER 1 -continued

| INCI name | % by weight |
|---|---|
| PHOSPHORIC ACID | 0.1 |
| ALUMINUM HYDROXIDE | 0.1 |
| SORBIC ACID | 0.1 |
| HYDROGENATED POLYISOBUTENE | 0.1 |

POWDER 2

| INCI name | % by weight |
|---|---|
| TALC | qs 100 |
| SYNTHETIC FLUORPHLOGOPITE | 25.3 |
| PIGMENTS AND NACRES | 7.2 |
| SILICA | 12 |
| ETHYLHEXYL METHOXYCINNAMATE | 9.5 |
| ETHYLENE/ACRYLIC ACID COPOLYMER | 5.0 |
| BORON NITRIDE | 4.0 |
| MAGNESIUM ASCORBYL PHOSPHATE | 3.2 |
| POLYMETHYL METHACRYLATE | 2.0 |
| PENTYLENE GLYCOL | 1.0 |
| WATER | 0.85 |
| SODIUM DEHYDROACETATE | 0.45 |
| ISOPROPYL TITANIUM TRIISOSTEARATE | 0.3 |
| TETRASODIUM EDTA | 0.2 |
| DIMETHICONE/METHICONE COPOLYMER | 0.15 |
| ALUMINUM HYDROXIDE | 0.1 |
| SORBIC ACID | 0.1 |
| HYDROGENATED POLYISOBUTENE | 0.1 |

The study involved 10 subjects.

The protocol and conditions for measuring the sun protection index are those given in the method "International Sun Protection Factor Test Method—2006" published by Colipa, with the exception of the following parameters:

dose applied (0.8 mg/cm$^2$), time elapsed between the application of product and the measurement (5 min).

Since the protocol differs here from the "International Sun Protection Factor Test Method—2006" measuring method published by Colipa, reference is no longer made to the SPF, but to a sun protection index, in order to characterize the protection conferred against UV rays by these compositions.

When the products are superposed, each product is allowed to dry for 5 minutes before applying the next product.

Table 1 gives the protection indices measured for each composition, according to the protocol specified above.

TABLE 1

Measurement of the sun protection index of the compositions used for the study

| Composition tested | Protection index |
|---|---|
| CARE BASE 1 | 12.2 +/− 2.0 |
| CARE BASE 2 | 2.1 +/− 0.2 |
| POWDER 1 | 4.0 +/− 0.7 |
| POWDER 2 | 4.0 +/− 0.7 |
| FOUNDATION 1 | 16.4 +/− 2.5 |
| FOUNDATION 2 | 3.6 +/− 0.5 |

Table 2 gives the protection indices measured according to the protocol above (unless otherwise mentioned in the tables), after successive application to the skin of two or three compositions tested, according to the order specified in the table.

TABLE 2

Measurement of the sun protection index of the superposition of two or three compositions according to the invention

| Steps carried out | Protection index |
|---|---|
| Superposition of CARE BASE 1, of FOUNDATION 1 and then of POWDER 1 Comparative test 1 | 41.9 +/− 5.0 |
| Superposition of CARE BASE 1 then of FOUNDATION 1 Comparative test 2 | 29.6 +/− 3.4 |
| Mixture of the three products (CARE BASE 1, FOUNDATION 1 and POWDER 1) applied in a layer of 2.4 mg/cm$^2$ | 25.3 +/− 4.1 |
| Superposition of CARE BASE 1 then of POWDER 1 | 19.4 +/− 3.2 |
| Superposition of CARE BASE 2 then of POWDER 2 | 8.1 +/− 1.4 |
| Superposition of FOUNDATION 1 then of POWDER 1 | 31.5 +/− 4.1 |
| Superposition of Ia CARE BASE 2 then of POWDER 1 | 10.2 +/− 1.6 |
| Superposition of FOUNDATION 2 then of POWDER 1 | 11.0 +/− 1.4 |

Results

The deposit of the mixture of three products (care base, liquid foundation and powder) has a sun protection index that is lower than that of the deposit formed by the superposition of the three products taken separately. The mixture of the three products is very viscous and does not have satisfactory sensory properties which allow its application to the skin. The sun protection index of the deposit resulting from the superposition of the three products is therefore higher both i) than the sum of the sun protection indices of the deposits of each of the products applied individually and ii) than the sun protection index of the deposit of the mixture of the three products, in equal deposit amounts.

The method of the invention makes it possible to improve the protection of the skin against UV rays while improving the sensory properties of the cosmetic product.

The sun protection index obtained by the superposition of the two products according to the method of the invention is statistically significantly higher than the sum of the two individual sun protection indices.

The invention claimed is:

1. A method for protecting human skin from ultraviolet (UV) rays, the method comprising:
   (1) topically administering to the skin of a human in need thereof a first cosmetic composition comprising an oil phase, an aqueous phase, and a UV-screening agent selected from the group consisting of benzophenone-4, methylene bis-benzotriazolyl tetramethyl butylphenol, and a mixture thereof, wherein the first cosmetic composition has a sun protection factor (SPF) of greater than 10, thereby forming a first UV-screening layer on the skin; and thereafter
   (2) topically administering on top of the first UV-screening layer a second cosmetic composition comprising an oil phase, a liposoluble organic UV-screening agent, and at least 70% by weight of powders selected from the group consisting of fillers, pigments, and mixtures thereof, wherein the second cosmetic composition is anhydrous and has an SPF of less than or equal to 10, thereby forming a second UV-screening layer on the skin; and
   wherein the liposoluble organic UV-screening agent is soluble in the oil phase of the second cosmetic composition and in the oil phase of the first cosmetic composition.

2. The method of claim 1, wherein the first cosmetic composition does not comprise an inorganic UV-screening agent selected from metal oxide pigments having an average particle size between 5 nm and 100 nm.

3. The method of claim 1, wherein the liposoluble organic UV-screening agent is ethylhexyl methoxycinnamate.

4. The method of claim 1, wherein the oil phase of the first cosmetic composition comprises cyclopentasiloxane.

* * * * *